United States Patent [19]

Kimoto

[11] Patent Number: 5,162,366
[45] Date of Patent: Nov. 10, 1992

[54] ANTIOXIDANT COMPOSITION IN VIVO COMPRISING ENOL FORM δ-LACTONE OF DIKETOGULONIC ACID

[75] Inventor: Eiji Kimoto, Fukuoka, Japan

[73] Assignee: Nissan Chemical Industries, Ltd., Tokyo, Japan

[21] Appl. No.: 645,487

[22] Filed: Jan. 24, 1991

[30] Foreign Application Priority Data

Jan. 26, 1990 [JP] Japan .................................. 2-17073
Aug. 28, 1990 [JP] Japan ................................. 2-226087

[51] Int. Cl.$^5$ ...................... A61K 31/35; A61K 49/00
[52] U.S. Cl. .................................. 514/460; 514/458; 424/10
[58] Field of Search ............... 514/455, 451, 458, 460; 424/10

[56] References Cited

FOREIGN PATENT DOCUMENTS 200684 8/1990 Japan .

OTHER PUBLICATIONS

CA114(9):82428e.

Primary Examiner—Frederick E. Wadell
Assistant Examiner—Diane Gardner
Attorney, Agent, or Firm—Oliff & Berridge

[57] ABSTRACT

Enol form δ-lactone of diketogulonic acid (2,3,6-trihydroxy-4-oxo-2-hexen-5-olide; R-345), which is the enediol type oxidation product of ascorbic acid, and/or its sodium salt, potassium salt or calcium salt has activities of markedly reducing the toxicity of Adriamycin, reducing radiation injury, reducing liver damage induced by an organic halogen compound, and further accelerating recovery from a high blood sugar level in Alloxan-induced diabetes, using vitanim E in combination.

8 Claims, 7 Drawing Sheets

ANTIOXIDANT COMPOSITION IN VIVO COMPRISING ENOL FORM δ-LACTONE OF DIKETOGULONIC ACID

BACKGROUND OF THE INVENTION

1. Field of the Invention

The present invention relates to an in vivo antioxidant composition comprising enol form δ-lactone of diketogulonic acid (2,3,6-trihydroxy-4-oxo-2-hexen-5-olide) and/or its sodium salt, potassium salt or calcium salt and more particularly, to a composition for reducing the toxicity of Adriamycin using in combination with vitamin E which is a fat-soluble antioxidant, a composition for reducing radiation injury using in combination with vitamin E, a composition for reducing disturbance due to lipid peroxidation in liver using in combination with vitamin E, a composition for reducing a peroxidized state in vivo, for example, a peroxidized state in vivo in Alloxan-induced diabetes, and a composition for reducing a peroxidized state in vivo in a broad sense.

The present invention also relates to a method for reducing or improving a peroxidized state in vivo by administering the aforesaid drug composition to mammal or human.

2. Description of the Prior Art

Anti-tumor agents such as Adriamycin generate activated oxygen to cause peroxidation in myocardiac tissue, etc. Due to these severe side effects, it is difficult to sufficiently enhance their therapeutic coefficient.

Most of radiation injuries are caused by peroxidation based on the oxygen effect: liver poison such as an organic halogen compound, etc. generates radicals to cause lipid peroxidation in liver, and Alloxan generates activated oxygen to cause peroxidation of pancreas β cells to lower the secretion of insulin (pancreas β cells show a high xanthine oxidase activity but have a low superoxide dismutase activity and it is generally considered that pancreas β cells would be one of cells most susceptible to peroxidation in vivo).

In order to reduce oxygen toxicity due to these peroxidation reactions, it has been attempted to use vitamin E, vitamin C, CoQ$_{10}$, glutathione and the like. However, no satisfactory effect has been obtained yet.

An antioxidant is generally a reducing agent and reacts with activated oxygen or radicals to eliminate them and on the other hand, itself is oxidized.

The oxidation product is reproduced to the original reduction type antioxidant by enzymatic or non-enzymatic "settling" effect, within the limit of injury in tissue cells. Where injury of tissue cells due to peroxidation is severe, however, the reproducing function is not sufficiently exhibited but the oxidation products produced from the antioxidant and harmful oxidation decomposition products or radicals produced therefrom cause secondary injury. This is regarded as drawbacks of conventional antioxidants.

Oxygen is difficultly soluble in an aqueous solution but readily soluble in the oil and fat phase. Components most susceptible to peroxidation in tissue cells are higher unsaturated fatty acids in the oil and fat phase of membrane. Accordingly, fat-soluble vitamin E plays an important role as an antioxidant in vivo. However, an extremely low amount of vitamin E can be retained in tissue cells and an excess amount of the vitamin E is rather disadvantageous. A sufficient antioxidant activity is not exhibited by the use of vitamin E alone.

Therefore, there is a theory that it would be necessary to utilize a synergistic effect or complementary effect using vitamin C in combination; vitamin C is a water-soluble antioxidant which is usable in large quantities. However, this theory is still insufficient. Vitamin C is fallen into a dilemma that it accelerates peroxidation in such a state that iron ions, copper ions, etc. are liberated, namely, in such a state that the "settling" effect is not sufficiently exhibited.

SUMMARY OF THE INVENTION

It has been surprisingly found that enol form δ-lactone of diketogulonic acid [2,3,6-trihydroxy-4-oxo-2-hexen-5-olide; hereafter referred to as R-345] represented by formula I:

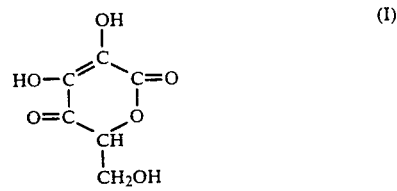

which is the enediol type oxidation product of ascorbic acid, and/or its sodium salt, potassium salt or calcium salt and which has activities of reducing tert-butyl hydroperoxide-induced lipid peroxidation of erythrocyte membrane, reducing the toxicity of Adriamycin, reducing radiation injury, reducing peroxidative state of the liver induced by an organic halogen compound, and further accelerating recovery from a high blood sugar level in Alloxan-induced diabetes. By using vitamin E in combination, remarkable antioxidative activities are noted by the synergistic effect.

Even by single use of R-345, it somewhat reduces the toxicity of Adriamycin, radiation injury and peroxidation of lipid in liver and is somewhat effective for recovery from a high blood sugar level in Alloxan-induced diabetes.

BRIEF DESCRIPTION OF THE DRAWINGS

In FIG. 4, the following abbreviations are used.
normal: control group
saline: physiological saline
AsA: ascorbic acid
VE: vitamin E
VE: AsA: VE and AsA in combination
VE: R-345: VE and R-345 in combination
●: measurement data on each mouse —: mean value of measurement data

DETAILED DESCRIPTION OF THE PREFERRED EMBODIMENTS

Figure 1:
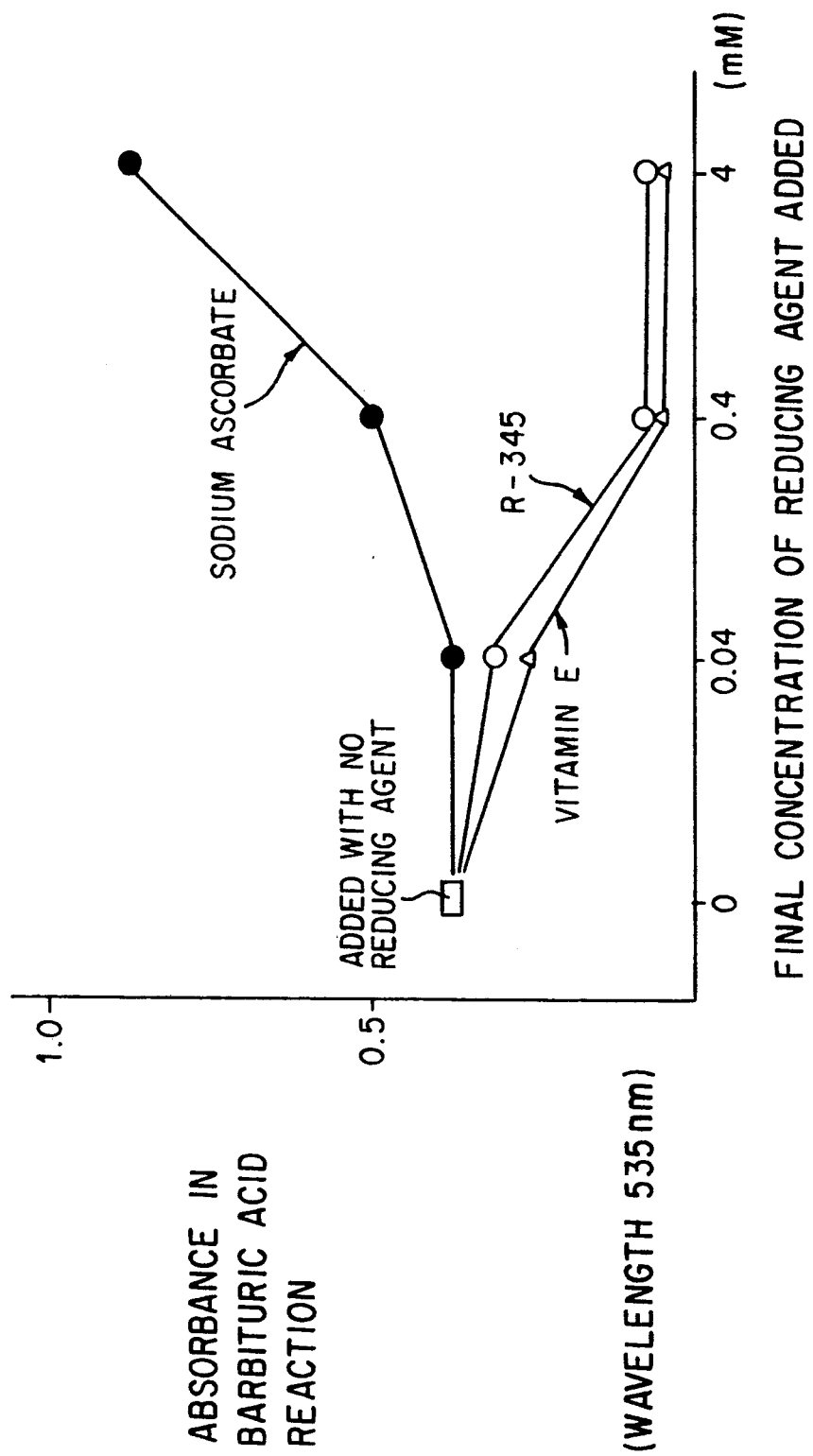
FIG. 1 shows influence of reducing agents on lipid peroxidation in erythrocyte membrane by tert-butyl hydroperoxide.
Figure 2A:
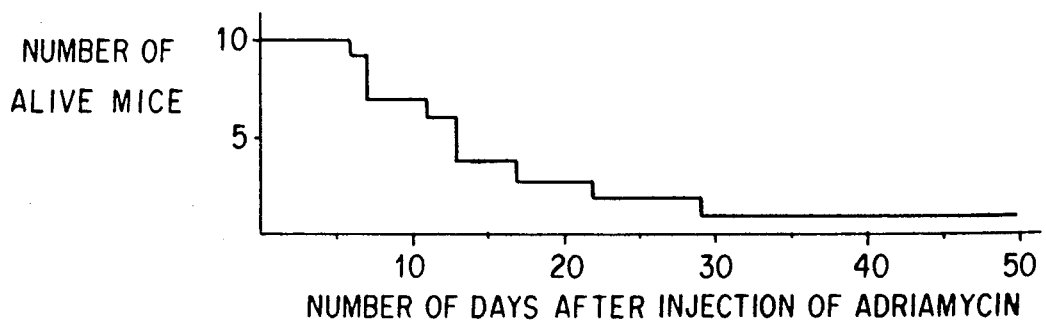
FIGS. 2 a) through d) show influence on increased life span after injection of Adriamycin when administered with R-345 alone, vitamin E alone and R-345 plus vitamin E in combination.
Figure 2B:
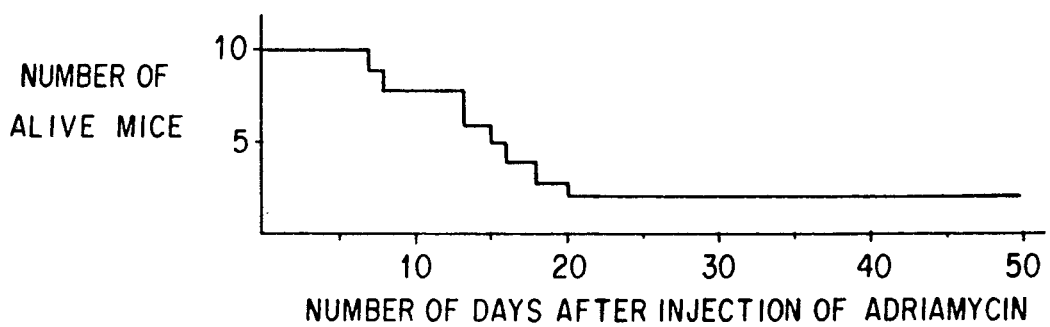
Figure 2C:
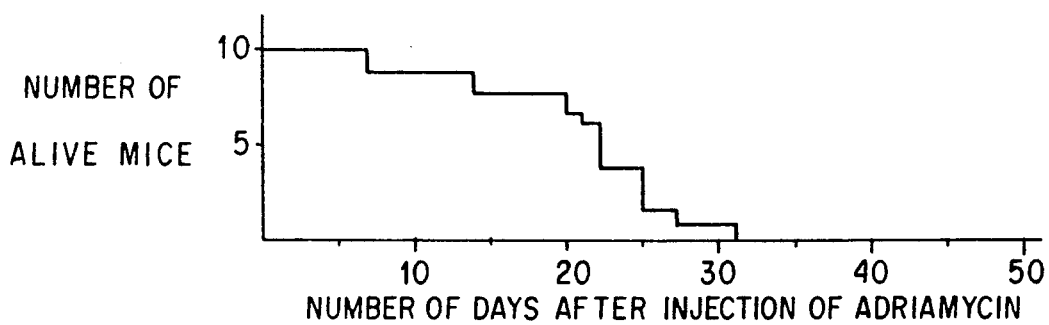
Figure 2D:
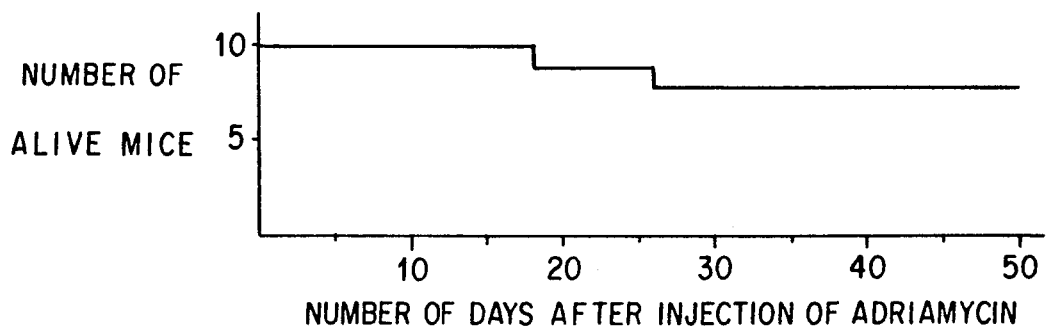
Figure 3A:
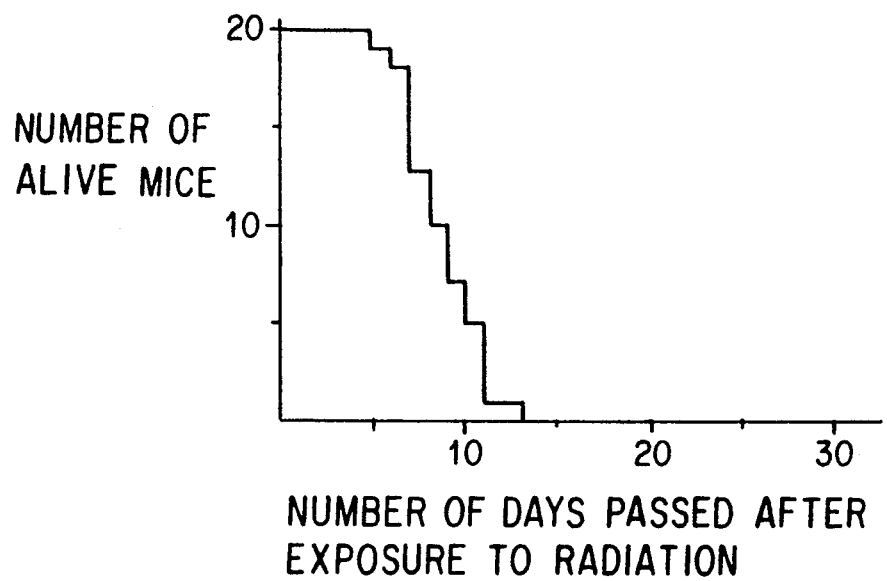
FIGS. 3 a) through d) show influence on increased life span after exposure to radiation when administered with R-345 alone, vitamin E alone and R-345 plus vitamin E in combination.
Figure 3B:
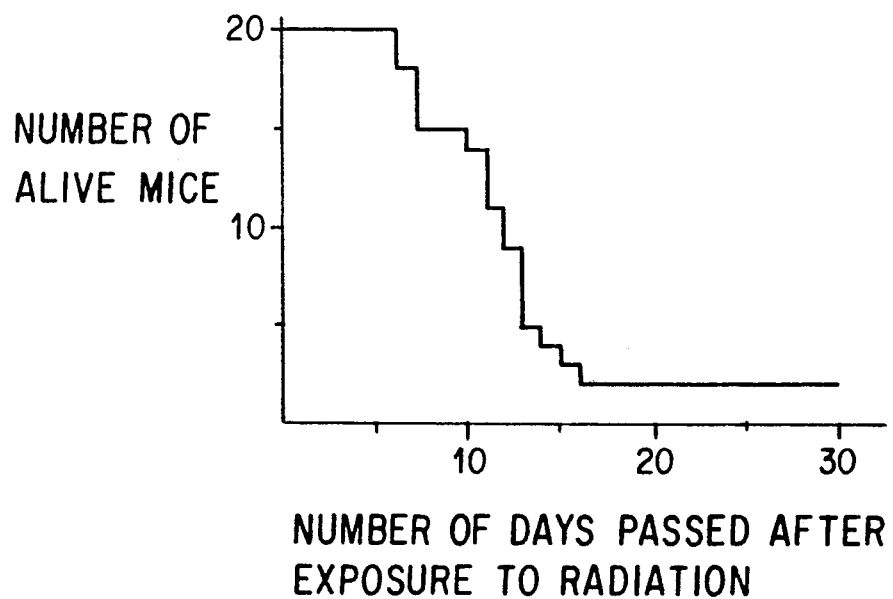
Figure 3C:
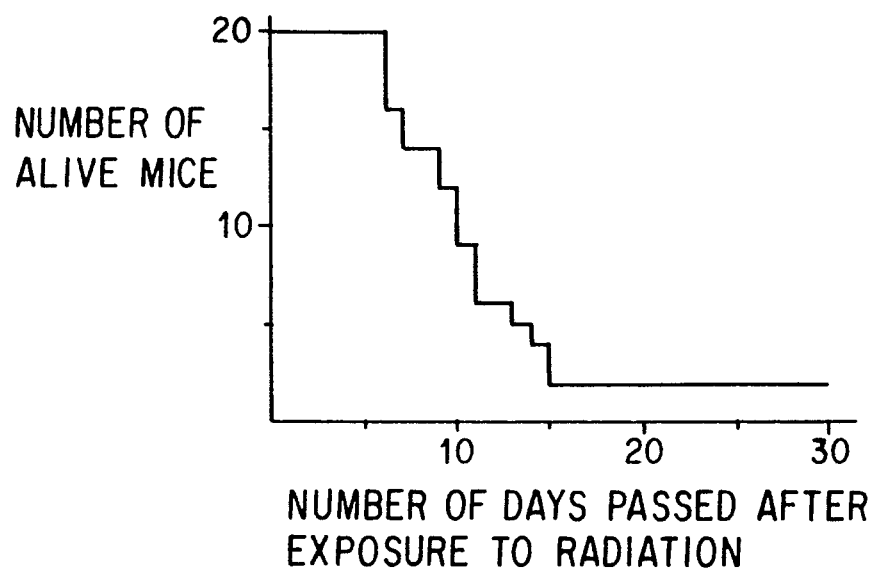
Figure 3D:
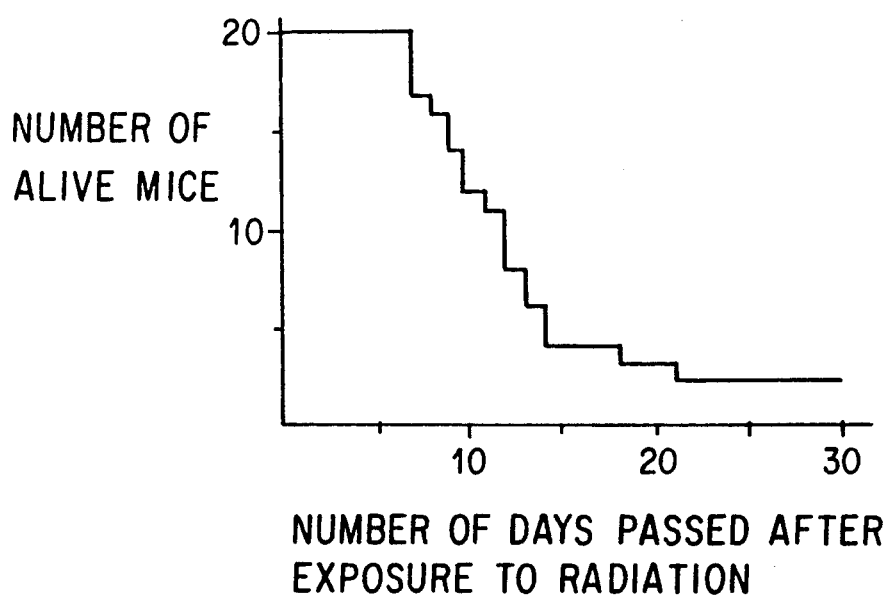
Figure 4A:
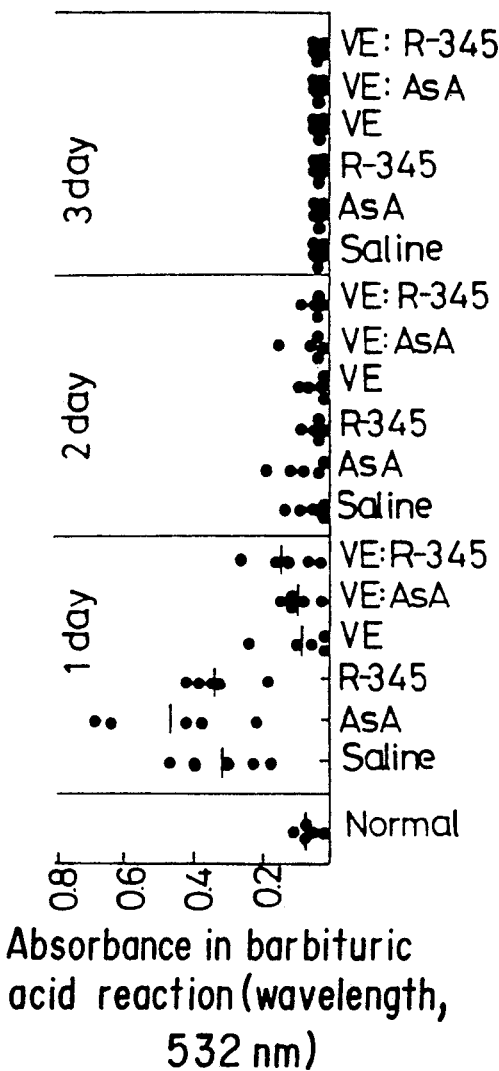
FIGS. 4 a) through c) show influence on hepatic disturbance induced by organic halogen compounds when administered with R-345 alone, ascorbic acid alone, vitamin E alone and combination use thereof.
Figure 4B:
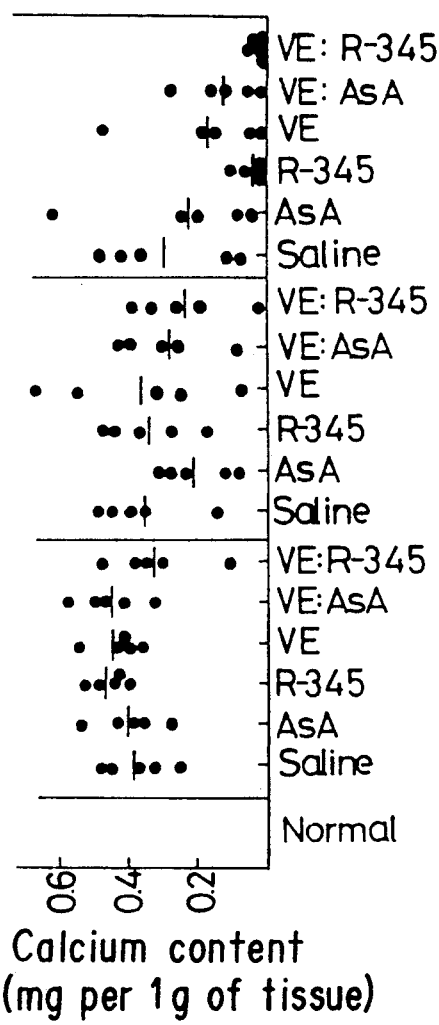
Figure 4C:
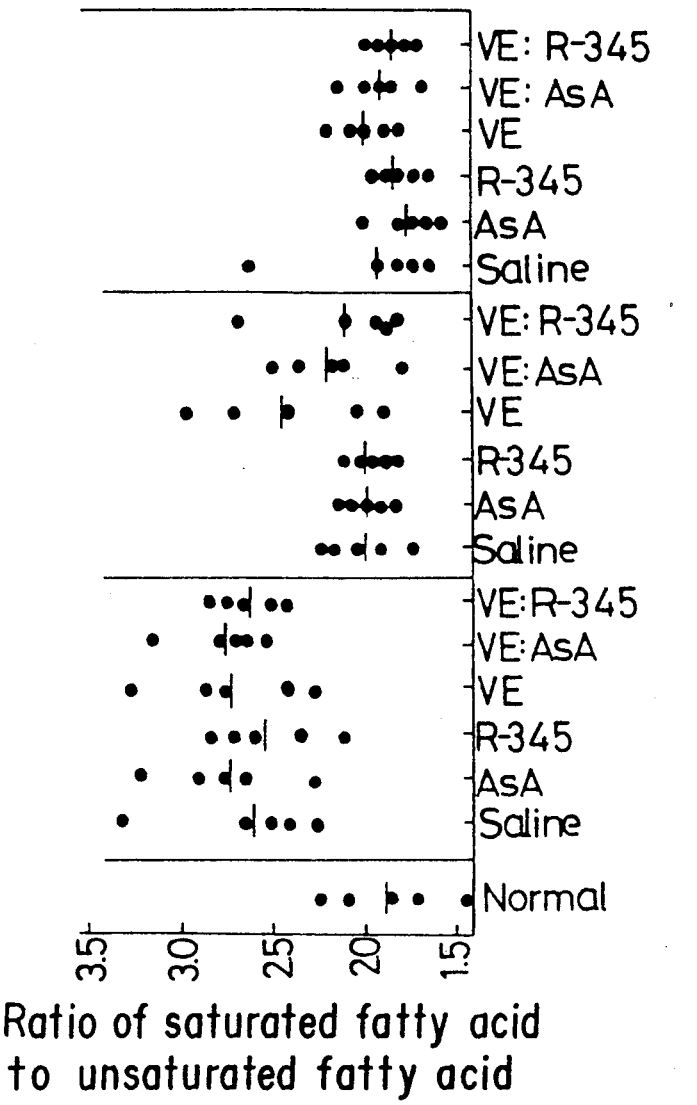
Figure 5:
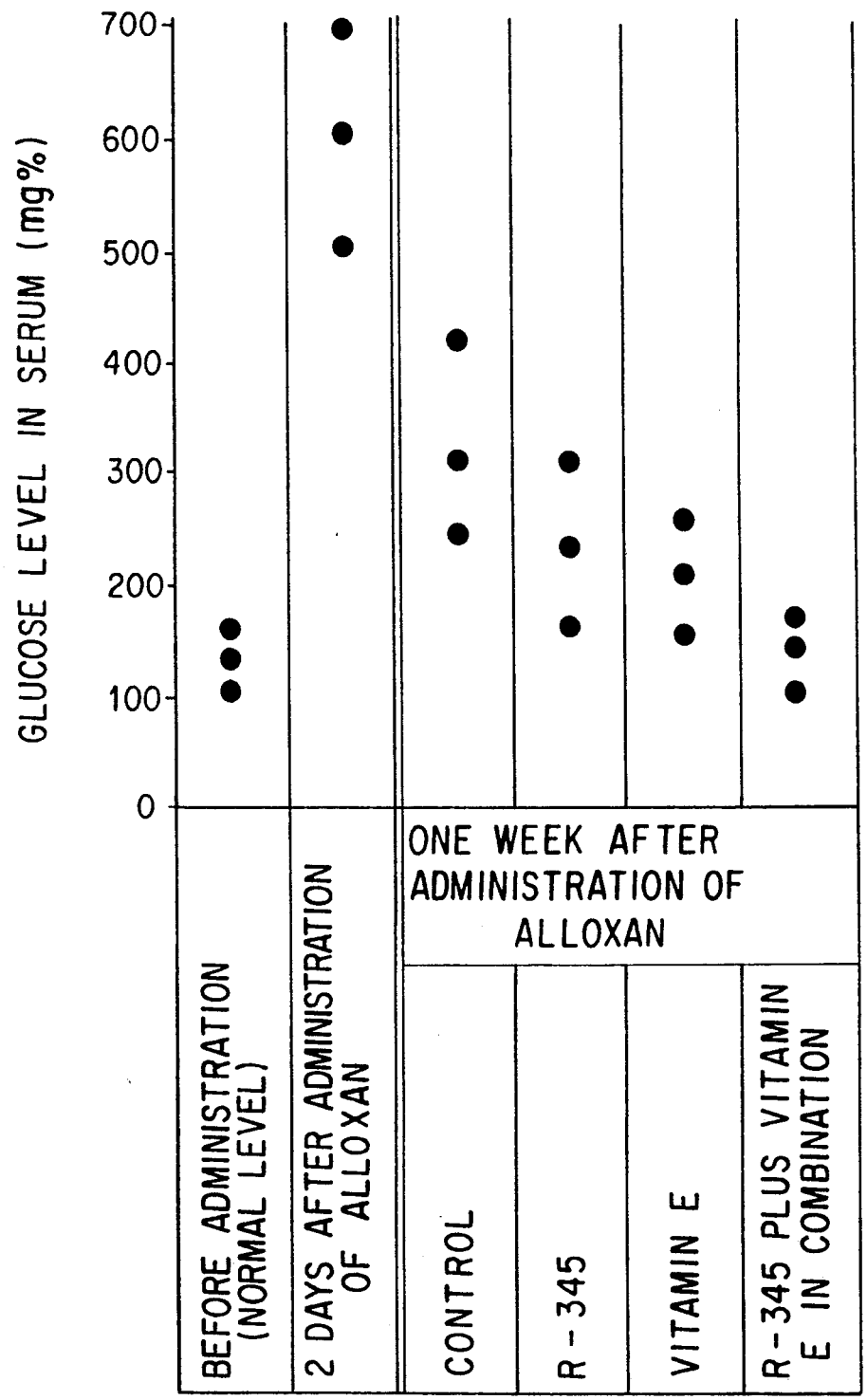
FIG. 5 shows influence on recovery of hyperglycemia in Alloxan-induced diabetes when administered with R-345 alone, vitamin E alone and R-345 plus vitamin E in combination.

Adriamycin used in the present invention is not limited only to Adriamycin but also includes analogues of Adriamycin which show activities similar to anti-cancer activity and side effects (toxicity) noted when Adriamycin alone is administered.

The present invention also applies to anti-tumor agents such as Bleomycin or Mitomycin C which generates activated oxygen to cause side effects.

Vitamin E used in the present invention refers to compounds having the same basic skeleton as that of α-tocopherol and means compounds having a vitamin E-like antioxidation activity. That is, in addition to vitamin E, it also includes vitamin E esters such as vitamin E acetate (α-tocopherol acetate).

Radiation injury is used to mean not only injury caused by exposure to radiation in radio-diagnosis of radiotherapy but also injury caused by accidental exposure to radiation.

In this radiation injury, exposure to radiation in a large dose definitely requires urgent care. For example, where bone marrow transplantation is required, it takes several days for compatibility test prior to transplantation since storage of self bone marrow by freezing has not yet spread. Therefore, if conditions of the patient exposed to radiation are alleviated and the effect of increasing life span is exerted even for 2 or 3 days, it would be very advantageous. By using R-345, etc. in combination with vitamin E, the effect of increasing life span can be improved (cf. Example 3).

In addition, R-345 and the like sufficiently exhibit the antioxidation activity against diseases accompanied by peroxidation in vivo, for example, hepatic disturbance induced by organic halogen compounds (liver poison) such as Halothane, reduction in insulin secretion ability of pancreatic β cells induced by peroxidation accelerators such as Alloxan, ischemia, inflammation, etc.

It is noted that R-345, etc. tends to be decomposed some or less when it is put in water over a long period of time. Therefore, it is generally used to dissolve R-345, etc. in water immediately before use. It is preferred to use R-345, etc. in the form of injection.

R-345, etc. are usually stored in a dry state just before it is provided for use. In order to avoid contact with any substance to cause oxidation in the air, e.g., oxygen, R-345, etc. may be stored in an inert gas, e.g., carbon dioxide gas, nitrogen gas, helium gas or a gaseous mixture thereof, in a sealed state, under normal pressure or such a pressure that is a little bit or somewhat higher than normal pressure.

R-345 which is the form of solid or an aqueous solution may be preferably stored in a refrigerator prior to use.

R-345, etc. can be administered in the form of an oral drug, an external drug, a suppository or an injection but may be often used in the form of an injection.

Upon use, pH value of R-345, etc. is generally in a range of 7.0 to 7.2. When it is used as an injection, pH value of the liquid containing R-345, etc. is generally in a range of 7.0 to 7.2.

Where R-345, etc. may be administered as an injection, sites administered may be subcutaneous, intramuscular, intravenous, intraarterial, intraperitoneal, etc. Preferably R-345, etc. may be administered intravenously.

R-345, etc. may be preferably administered by mixing them with supplementation fluids such as Ringer's solution, amino acid nutrient fluid, oligopeptide nutrient fluid, other nutrient supplementing fluids, physiological saline, etc.; or solutions of drugs such as anti-tumor solutions (e.g., Adriamycin, Mitomycin C, etc.), solutions of antibiotics (e.g., β-lactams or antibiotics or of penicillin type or cephem type, or Amphotericin B); [hereafter these solutions or fluids are referred to as Ringer's solution, etc.].

Where R-345, etc. are mixed with Ringer's solution, etc., the concentration varies depending upon daily dose described below but is generally about 0.1 to 1.0%.

Where Adriamycin used in combination with vitamin E is locally administered or a site exposed to radiation is localized, it is sometimes preferred to administer R-345, etc. in such a manner that R-345, etc. may be present at the site relatively densely. In this case, the application follows its conventional manner. For example, the manner may be that after intravenous injection or subcutaneous administration in the form of a tablet or a capsule, R-345, etc. is gradually released.

In the case that the localized site is mucous membrane (e.g., sublingual), it may be possible to administer an adhesive and multi-coated tablet (e.g., lozenge).

Toxicity of R-345, etc. is very low. For example, in the case of ddY strain female mouse, no toxicity was shown even though monosodium salt of R-345 was intraperitoneally administered in a dose of 1,000 mg/kg.

A daily dose of R-345, etc. may vary depending upon kind and dose of anti-tumor agent administered and dose of radiation. The daily dose may also vary depending upon sex, body weight, age, condition, etc. of patient.

The dose of R-345 increases as the dose of anti-tumor agent and the dose of radiation increase.

In general, the dose is in a range of 0.1 to 2.0 g/60 kg of body weight; if it is particularly limited, the dose is about 0.5 to about 1.0 g/60 kg of body weight. However, the dose is not limited to the above range.

A ratio of vitamin E used in combination to reduce the toxicity of Adriamycin to Adriamycin is generally (50:1) to (100:1).

A ratio of vitamin E administered to R-345, etc. is generally (1:1) to (1:5), preferably about (1:2).

Hereafter the present invention is described in detail by referring to preparation example and test examples. However, the present invention is not limited to the following test examples.

PREPARATION EXAMPLE 1

An aqueous solution of R-345 (pH value of 7.0 to 7.2) obtained in a manner similar to the method of Kimoto et al. [Fukoka University Science Reports, 18 (2), 149–158 (1989)] was freeze dried and the resulting solid was sealed in ampoules under nitrogen flow. An amount sealed per ampoule was 500 mg.

Upon use the ampoule may be unsealed, added to and dissolved in Ringer's solution, which is then provided for use.

Sodium salt of R-345 used in the following test example is sodium salt of R-345 obtained in Preparation Example described above. Upon use, it is dissolved in physiological saline to form a solution of about 0.5% (except for Test Example 1). As other active components, vitamin E was used as it was or dissolved in liquid paraffin and ascorbic acid was dissolved in physiological saline to form a solution of about 0.5%.

TEST EXAMPLE 1

Protecting Action of Erythrocyte Membrane (Activity on Inhibition of Peroxidation of Erythrocyte Membrane)

Human blood cells were subjected to hemolysis and red ghost (membrane segments containing hemoglobin) was collected by a centrifuging machine. To 0.25 ml of the suspension of red ghost (containing 200 mg % protein) were added 10 mmols (0.05 ml) of tert-butyl hydroperoxide, which was a peroxidizing agent, and 0.2 ml each of ascorbic acid (vitamin C) of various concentrations, vitamin E (dispersed in an aqueous solution of 1% sodium dodecylsulfate) or R-345. After the mixture was kept at 37° C. for 30 minutes, the resulting lipid peroxide was reacted with thiobarbituric acid. The reaction product was quantitatively determined by colorimetry at 535 nm.

By the addition of tert-butyl hydroperoxide, ascorbic acid was immediately oxidized so that absorption intensity at 265 nm was markedly reduced. However, R-345 was hardly oxidized and reduction in absorption intensity at 345 nm was slight.

As shown in FIG. 1, the amount of lipid peroxide increased with ascorbic acid but vitamin E and R-345 exhibited the activity of inhibiting the formation of peroxide. Even using ascorbic acid and vitamin E in combination, the formation of peroxide was almost the same as a mean value of both. In the case of using R-345 and vitamin E in combination, oxidation of lipid was completely prevented.

That is, it is considered that R-345 is more effective than ascorbic acid as a water-soluble antioxidant having the activity of alleviating erythrocyte membrane disturbance induced by a peroxidant.

TEST EXAMPLE 2

Activity of Reducing Toxicity of Adriamycin

Adriamycin ($LD_{50}=14$ mg/kg) was intraperitoneally administered to female ddY strain mice of 4 week age having a mean body weight of 25 g. Influence of each drug on survival days was thus examined.

FIG. 2a

Mice intraperitoneally administered with physiological saline for control group began to die on or after Day 5. Nine out of 10 mice died within 30 days and only one mouse survived longer than 50 days.

FIG. 2b

In the group intraperitoneally administered with R-345 (30 mg/kg) 4 times in total, i.e., on the day when Adriamycin was injected and then for the following 3 days, 8 out of 10 mice died up to about Day 20 and only 2 mice survived longer than 50 days. While a slight difference was observed between the control group and the group administered with R-345, such a marked difference as noted in the administration in combination with vitamin E later described was not noted.

FIG. 2c

In the group intraperitoneally administered with vitamin E (200 mg/kg) 4 times in total, i.e., on the day before Adriamycin was injected, the day when Adriamycin was injected and then for the following 2 days, mice died with almost the same incidence as noted with the control group. None was survived longer than 31 days.

FIG. 2d

In the group intraperitoneally administered with R-345 (30 mg/kg) and vitamin E (200 mg/kg) in combination, only 2 out of 10 mice died within 30 days but 8 mice survived longer than 50 days. Most of the survived mice showed increased body weight as compared to the time when the test was started.

CONCLUSION

That is, by single administration of either vitamin E or R-345 alone, only a slight prolongation of survival days was noted but by using both in combination, remarkable prolongation of survival days was noted by the synergistic effect.

TEST EXAMPLE 3

Activity of Reducing Radiation Injury

Female ddY strain mice of 4 week age having a mean body weight of 25 g were exposed to X rays of 800 roentgen to examine the number of survival days (dose of $LD_{50}$ for 30 days was 407 to 466 roentgen).

FIG. 3a

In the group intravenously administered with physiological saline for control group began to die on or after Day 5. Almost all mice died in within 10 days. The longest survival days were 13 days and an average number of survival days was 8.7 days.

FIG. 3b

R-345 (285 mg/kg) was intravenously administered through the tail immediately before exposure to radiation, and on Days 1 and 3 (3 times in total). In the group administered with R-345, 3 out of 20 mice survived on Day 15 and 2 survived longer than 30 days. An average number of survival days was 12.9 days. With respect to a mouse survived longer than 30 days, the number of survival days was counted as 30 days to determine the average number of survival days.

When compared with the control group administered with physiological saline, there was a slight increase in terms of the average number of survival days.

FIG. 3c

Vitamin E (200 mg/kg) was intramuscularly administered 3 days and 1 day before exposure to radiation, and immediately before the exposure (3 times in total). In the group administered with vitamin E, 2 out of 20 mice survived on Day 15 and the 2 mice survived longer than 30 days. An average number of survival days was 11.8 days.

FIG. 3d

In the group administered with vitamin E and R-345 in combination, 4 out of 20 mice survived on Day 15 and 3 mice survived longer than 30 days. An average number of survival days was 13.4 days. That is, administration of vitamin E and R-345 in combination was most effective and the life span was increased longer by 1.5 times or more than the average number of survival days in the control group.

TEST EXAMPLE 4

Activity of Reducing Liver Toxicity by Organic Halogen Compounds

In liquid paraffin were dissolved 0.0025 ml of carbon tetrachloride ($CCl_4$) and 0.0050 ml of chloroform ($CHCl_3$) to form 0.1 ml of a solution. The solution was intraperitoneally administered to female ddY strain mice of 4 week age having a mean body weight of 25 g. With passage of day, concentration of lipid peroxide (TBA value, by thiobarbituric acid reaction), calcium concentration and a ratio of saturated fatty acids to unsaturated fatty acids (as an index of fatty liver), in liver were measured over 3 days.

Vitamin E (VE) (4 mg was dissolved in 0.1 ml of liquid paraffin) was intramuscularly injected the day before $CCl_4:CHCl_3$ was administered and then intraperitoneally administered immediately after administration of $CCl_4:CHCl_3$. Ascorbic acid (AsA) and R-345 (4 mg each was dissolved in 0.1 ml of physiological saline, respectively) were intraperitoneally administered once a day every day from 6 hours after $CCl_4:CHCl_3$ was administered to the day before the mice were sacrificed.

FIG. 4a

On Day 1 after administration of $CCl_4:CHCl_3$, TBA value increased in any group. In the group administered with AsA alone, some were higher than in the group administered with physiological saline (control group). By administration of R-345 alone, increase in TBA value was almost the same as in the control group. In the group administered with VE, TBA value in both groups administered with AsA or R-345 in combination was lower than in the control group. It was thus noted that VE was effective for preventing the increase in TBA value.

FIG. 4b

Calcium content increased in all groups on Day 1 after administration of $CCl_4:CHCl_3$. Even on Days 2 and 3, the calcium content was not readily reversed to normal level. However, the calcium content was almost recovered to normal level in the group administered with R-345 alone and in the group administered with VE : R-345 in combination, although the calcium content was not lowered to normal level in the group administered with AsA, with VE or with AsA:VE in combination.

That is, VE prevented an increase in TBA value (peroxidation of lipid) but the activity of preventing the increase of calcium level was not noted with VE.

FIG. 4c

A ratio of saturated fatty acid to unsaturated fatty acid considerably increased on Day 1 after administration. The ratio was less than 2.0 in normal liver and about 3.5 in adipose tissues. However, the ratio of $CCl_4:CHCl_3$ damaged livers was close to the latter in some cases. In spite, it is regarded that there is no significant difference among the six groups. However, on Day 2, it appears that in the group administered with VE, recovery would be slower than in the group administered with no VE. It also appears, however, that in the group administered with AsA or R-345 in combination, recovery would be slightly quicker than in the group administered with VE alone. On Day 3, the ratio was recovered to normal level in all groups.

CONCLUSION

The activity of 3 antioxidants, R-345, ascorbic acid and vitamin E for reducing hepatic disturbance in mice by administration of $CCl_4:CHCl_3$ was examined and the following results were obtained.

On the day following the administration of $CCl_4:CHCl_3$, TBA value increased; in the group administered with ascorbic acid, particularly high TBA value was noted in some cases.

In vitamin E, the effect of preventing increase in TBA value (lipid peroxide level) was noted. However, a tendency to delay the recovery to normal level of calcium content on Day 3 after administration of $CCl_4:CHCl_3$ was noted.

In the group administered with R-345 alone and the group administered with vitamin E and R-345 in combination, especially in the latter group, increase in TBA value, calcium content and increase in neutral fat was reduced as compared to the control group or the group administered with vitamin E alone.

It has thus been found that water-soluble antioxidant, R-345, shows the synergistic effect with or complementary effect to fat-soluble antioxidant, vitamin E.

TEST EXAMPLE 5

Effect of Recovery from Hyperglycemia in Alloxan-Induced Diabetes

After Alloxan (80 mg/kg) was intravenously administered to female ddY strain mice of 4 week age showing a mean body weight of 25 g, 0.2 ml of vitamin E solution (dissolved in liquid paraffin in a concentration of 5%) was intramuscularly injected per mouse once a day from the next day and 0.2 ml of R-345 (dissolved in physiological saline in a concentration of 2 wt %) was intraperitoneally injected. In the control group, 0.2 ml of physiological saline was intraperitoneally injected per mouse. Blood sugar level was measured one week after administration of Alloxan.

FIG. 5

On Day 2 after administration of Alloxan, blood sugar level (glucose level) increased to 500 mg % or more and this high level (250 to 400 mg %) was maintained even after one week. Even though R-345 or vitamin E was given singly, the blood sugar level still showed a level somewhat higher than normal level. However, when R-345 and vitamin E were administered in combination, the blood sugar level was lowered to almost normal level.

CONCLUSION

To repair in a peroxidized state in Alloxan-induced diabetes, administration of R-345 and vitamin E in combination was effective; it was shown by animal experiment using as an index the recovery of high blood sugar level to normal level.

R-345 which is the enediol form oxidation product of ascorbic acid and/or its sodium salt, potassium salt or calcium salt can prevent the peroxidation of lipid in red blood cell membrane caused by peroxidizing agents, unlike ascorbic acid, and can exhibit the activity of reducing toxicity of Adriamycin, radiation injury and liver damage by organic halogen compounds to a considerable degree, by the synergistic effect with fat-soluble antioxidant, vitamin E. R-345, etc. also accelerated recovery of high blood sugar level in Alloxan-induced diabetes to normal level.

This R-345 is useful as an antioxidant for improving the morbid condition of the living body which has become an excessively peroxidized state, and as an effective ingredient in therapeutic compositions supplemental or complementary to other therapy.

While the invention has been described in detail and with reference to specific embodiments thereof, it is apparent to one skilled in the art that various changes and modifications can be made therein without departing from the spirit and the scope of the present invention.

What is claimed is:

1. An in vivo antioxidant composition comprising enol form δ-lactone of diketogulonic acid (2,3,6-trihydroxy-4-oxo-2-hexen-5-olide) represented by formula I:

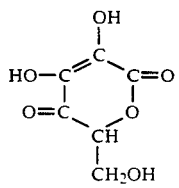

(I)

and/or its sodium salt, potassium salt or calcium salt and at least one pharmaceutically acceptable carrier.

2. A process comprising administering to a mammal an in vivo antioxidant composition comprising enol form δ-lactone of diketogulonic acid (2,3,6-trihydroxy-4-oxo-2-hexen-5-olide) represented by formula I:

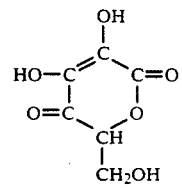

in an amount to thereby treat or prevent a peroxidation state in said mammal.

3. The process as claimed in claim 2, wherein said composition protects erythrocyte membrane from peroxidation.

4. The process as claimed in claim 2, wherein said composition reduces the toxicity of an Adriamycin agent, used in combination with a vitamin E.

5. The process as claimed in claim 2, wherein said composition reduces radiation injury, used in combination with a vitamin E.

6. The process as claimed in claim 2, wherein said composition reduces the disturbance induced by lipid peroxidation in liver, used in combination with a vitamin E.

7. The process as claimed in claim 2, wherein said composition reduces the in vivo peroxidation state in Alloxan-induced diabetes.

8. The process recited in claim 2, wherein said composition reduces or improves a peroxidized state in vivo.

* * * * *